United States Patent [19]

Kauffmann

[11] Patent Number: 5,569,465
[45] Date of Patent: Oct. 29, 1996

[54] AQUEOUS COSMETIC OR DERMO-PHARMACEUTICAL COMPOSITION CONTAINING IN SUSPENSION HYDRATED SPHEROIDS OF A HYDROPHILIC LIPIDIC SUBSTANCE

[75] Inventor: Myriam Kauffmann, Lyons, France

[73] Assignee: L'Oreal, Paris, France

[21] Appl. No.: 450,083

[22] Filed: May 25, 1995

Related U.S. Application Data

[63] Continuation of Ser. No. 678,870, Apr. 4, 1991, Pat. No. 5,532,000.

[30] Foreign Application Priority Data

Apr. 5, 1990 [FR] France .................................. 90 04387

[51] Int. Cl.⁶ .................................................. A61K 9/127
[52] U.S. Cl. ........................ 424/450; 514/772; 514/784; 514/785; 514/786; 514/939; 514/941; 514/943
[58] Field of Search .......................... 424/450; 514/772, 514/784, 785, 786, 941, 943, 939

[56] References Cited

U.S. PATENT DOCUMENTS

| | | |
|---|---|---|
| 4,217,344 | 8/1980 | Vanlerberghe . |
| 4,244,942 | 1/1981 | Kamishita et al. . |
| 4,375,480 | 3/1983 | Soma . |
| 4,511,563 | 4/1985 | Schmolka . |
| 5,004,598 | 4/1991 | Lochhead et al. . |

FOREIGN PATENT DOCUMENTS

| | | |
|---|---|---|
| 0069423 | 1/1983 | European Pat. Off. . |
| 0224457 | 6/1987 | European Pat. Off. . |
| 0275358 | 7/1988 | European Pat. Off. . |
| 2204792 | 11/1988 | United Kingdom . |

OTHER PUBLICATIONS

Remington's Pharmaceutical Sciences 15th ed., Mack Publishing Co., Easton, PA, pp. 327–339 (1975).

*Primary Examiner*—Marianne M. Cintins
*Assistant Examiner*—M. Moezie
*Attorney, Agent, or Firm*—Cushman Darby & Cushman, L.L.P.

[57] ABSTRACT

An aqueous cosmetic or dermo-pharmaceutical composition contains, in suspension in the continuous phase, hydrated spheroids of a hydrophilic lipidic substance. The hydrated spheroids have an average particle diameter ranging from 50 to 10,000 μm. A process for the preparation of this composition is described.

4 Claims, No Drawings

AQUEOUS COSMETIC OR DERMO-PHARMACEUTICAL COMPOSITION CONTAINING IN SUSPENSION HYDRATED SPHEROIDS OF A HYDROPHILIC LIPIDIC SUBSTANCE

This is a continuation of application Ser. No. 07/678,870, filed Apr. 4, 1991, now U.S. Pat. No. 5,532,000.

The present invention relates to an aqueous cosmetic or dermo-pharmaceutical composition containing, in suspension, small hydrated spheres or spheroids of a hydrophilic lipidic substance. These spheroids can be charged with at least one liposoluble or nonliposoluble cosmetic or dermo-pharmaceutical component.

BACKGROUND OF THE INVENTION

Numerous topically applied compositions are formulated in aqueous form and they principally take the form of gels, lotions and emulsions. These composition are generally employed as makeup removers, tonics, slenderizing products, sunscreen compositions, after sun compositions, capillary products, hygiene products such as, particularly, hygiene products for the mouth such as dentifrices, as well as certain makeup products, such as mascaras.

These compositions and, in particular, those having a continuous aqueous phase are all highly desirable since their inclusion in water imparts an agreeable freshness sensation to skin and mouth mucous. Moreover they do not impart an oily appearance to the skin or hair.

However, it has been observed that these compositions exhibit certain disadvantages in that they can cause an uncomfortable drying effect on the skin. Besides, they are generally poorly tolerated by persons having normal appearing skin which tends to dryness.

Until now, very few studies have been undertaken with the purpose of attempting to remedy these disadvantages.

Besides, it is well known that certain cosmetic components and principally perfumes and essential oils cannot be introduced in significant amounts into gels or emulsions without destabilizing them.

However, compositions in the form of gels containing emulsion inclusions have recently been proposed but their preparation requires complex injection apparatus and it has been noted that after removal, the two phases are admixed in a very irregular manner at surface level of the composition remaining in the package.

GENERAL DESCRIPTION OF THE INVENTION

After various studies, it has now been noted that the disadvantages of prior compositions, namely, a drying effect, a lack of comfort and destabilization by certain active principles, can be resolved by the presence, in suspension, of hydrated spheroids of a hydrophilic lipidic substance.

The spheroids which are incorporated in a solid state for a better dispersion, are hydrated and swollen on contact with the aqueous phase thereby imparting to the compositions new properties, principally emollient and lubricating properties.

The hydrated spheroids of the hydrophilic lipidic substance prevents a drying effect of the skin and provides a very agreeable comfort sensation.

Moreover, the compositions containing these hydrated spheroids require no particular apparatus for their production. They are quite stable vis-a-vis mechanical stirring.

The present invention thus relates to a cosmetic or dermo-pharmaceutical aqueous composition containing, in suspension in the continuous phase, hydrated spheroids of a hydrophilic lipidic substance, the said hydrated spheroids having an average particle diameter between 50 and 10,000 µm.

The hydrated spheroids present in the composition of the present invention have a creamy consistency and can be compared to "pre-emulsions". They exhibit the characteristic, even in a medium of low viscosity (<50 cps) of not coalescing even in the case of stirring or dispensing the composition.

The cosmetic or dermo-pharmaceutical composition according to the present invention comprises essentially two phases, an external phase, i.e. a continuous phase which can be an emulsion, a gel or a lotion and an internal phase constituted by the hydrated spheroids which can be compared to small reservoirs or globules, sterically well defined, of a pre-emulsion or a thick cream having a strong lipidic content forming, during application to the skin, a very cosmetically agreeable emulsion with the external aqueous phase.

In accordance with the present invention and, in particular in the case of a gel or a lotion, the external phase can be water or a mixture of water and a hydroxylated organic solvent, such as, for example, ethyl alcohol, glycerine, glycols, such as propylene glycol or glycol ethers, such as the monoethylether of diethylene glycol. In this latter form of production, the aqueous mixture preferably contains at least 50 percent water.

When the continuous phase is an emulsion it is appropriate that the emulsifying agent, from a qualitative and quantitative viewpoint, is compatible with nonhydrated and hydrated spheroids, i.e. that it induces neither their dissociation nor their partial or total solubilization.

By the expression "spheroids", such as used in accordance with the present invention, is meant small essentially spherical solid particles whereas by the expression "hydrated spheroids" is meant small also essentially spherical creamy particles containing water.

The average diameter of the spheroids that are incorporated in the composition of the present invention can vary over wide limits, but it must be such that after hydration, the hydrated spheroids have an average particle diameter in the range indicated above and preferably between 100 and 5,000 µm.

As a function of the nature of the hydrophilic lipidic substance employed, the swelling of the spheroids by hydration has for an effect to increase, even to double, the average diameter of the said spheroids introduced into the composition.

In effect, the hydration capacity of the spheroids is such that they can absorb 1.3 to 8 times their weight of water, i.e. that their volume is multiplied by a factor between 1.3 and 8, if density differences are neglected. Consequently, their diameter is multiplied by the cube root of this factor, or 1.1 to 2.

On the other hand, the nature of the aqueous external phase and the temperature can modulate the absorption of water by the spheroids.

The weight percentage of spheroids introduced into the composition in the solid state is, however, a function of the desired effect; a high percentage imparting a more pronounced softening and lubricating effect.

In practice, this weight percentage is generally between 0.1 and 50 percent but preferably between 1.5 and 10 weight percent.

The hydrophilic lipidic substance employed in the formation of the spheroids must be solid at ambient temperature, i.e. exhibit a melting point greater than 20° C. The maximum melting point is not critical although it is preferred to use hydrophilic lipidic substances having a melting point lower than 80° C.

Representative particularly preferred solid hydrophilic lipidic substances employed for the preparation of the spheroids, include, principally:

(1) $C_{12}$–$C_{24}$ fatty alcohols having a melting point between 20° an 80° C. and having a hydroxyl index (OH I) between 100 and 300.

Among these fatty alcohols those particularly preferred are: myristic alcohol, cetyl alcohol and stearyl alcohol;

(2) partial esters of $C_{12}$–$C_{24}$ fatty acids with polyols or polyol oligomers such as ethylene glycol, propylene glycol, glycerol, linear, branched or cyclic $C_3$–$C_6$ sugars or diethylene glycol, polyethylene glycols, polyglycerols and saccharose.

These partial esters must have a melting point between 20° and 80° C. and a hydroxyl index (OH I) between 50 and 500 or an HLB (Hydrophile-Lipophile Balance) between 1 and 13.

Representative partial esters include principally: glycerol monodipalmitostearate, such as "GELEOL" sold by Gattefosse, sorbitan monopalmitate such as "ARLACEL 40" sold by ICI, diethylene glycol monostearate, such as "TEIGIN D" sold by Goldschmidt or glycerol behenate, such as "COMPRITOL", sold by Gattefosse;

(3) oxyethylenated derivatives of fatty bodies such as those of $C_{12}$–$C_{24}$ fatty alcohols and their esters, $C_{12}$–$C_{24}$ fatty acids and their esters, $C_{12}$–$C_{24}$ fatty amines and amides, and waxes, lanolins and hydrogenated oils and their mixtures, these fatty bodies being oxyethylenated with 2 to 50 moles of ethylene oxide (EO) per mole of fatty body.

These oxyethylenated derivatives of fatty bodies must have a melting point of 20° to 80° C. and an HLB between 1 and 13.

Representative ones include principally: stearyl alcohol oxyethylenated with 2 moles of ethylene oxide, such as "BRIJ 72" sold by ICI; polyethylene glycol distearate with 8 moles of ethylene oxide, such as "LIPOPEG 4 DS", sold by Lipo, or hydrophilic beeswax such as "APIFIL", sold by Gattefosse;

(4) products resulting from the alcoholysis reaction between triglycerides and polyoxyethylenated glycols, said products having a melting point between 20° and 80° C., and a hydroxyl index between 50 and 500 or an HLB between 1 and 13.

Of particular interest are glycolyzed polyoxyethylenated lauropalmitostearic glycerides (palm oil/interesterified hydrogenated palmiste), such as "LABRAFILS M2130BS, M2130CS and WL2514CS", sold by Gattefosse;

(5) phospholipids and sphingolipids and their hydrogenated derivatives having a melting point greater than 20° C., a hydroxyl index between 50 and 500 or an HLB between 1 and 13; and (6) amphiphilic silicones, such as dimethicone copolyols, polyalkyl dimethicone polyols, or their derivatives having long chain esters having 2 to 50 moles of ethylene oxide per mole of product, and having a melting point between 20° and 80° C.

The hydrophilic lipidic substances listed above can be employed alone or optionally in the form of a mixture thereof.

It is also possible to use mixtures of lipidic substances, each of them capable of having one or more characteristics (melting point, hydroxyl index, HLB) outside the previously defined limits, but whose combination possesses the stated physico-chemical characteristics.

It is also possible to adjust the consistency or the viscosity of the spheroids by introducing into the mixture, modified clays or an oily dispersion thereof, silicas, metallic soaps or any other structuring fatty body.

In accordance with one preferred embodiment of the present invention, the spheroids of hydrophilic lipidic substance contain dissolved or dispersed in their matrix, cosmetic or dermo-pharmaceutical components.

In accordance with this embodiment, the hydrophilic lipidic substance of the spheroids serves as a support and vehicle for components such as perfumes, essential oils or their constituents, pigments, fillers, dyes, vitamins, enzymes and various other active substances in the cosmetic sense which can be present in an amount of 0.01 to 70 percent and preferably from 1 to 40 percent by weight relative to the weight of the spheroids.

Thus, when such cosmetic or dermo-pharmaceutical components are incorporated in the spheroids of hydrophilic lipidic substances, it is convenient to select an appropriate hydrophilic lipidic substance so that after granulation, the spheroids are always provided in solid form before their incorporation in the composition, and they always retain their water absorption capacity.

The incorporation of perfume and essential oils in the spheroids is particularly appropriate for it is well known that these are destabilization factors.

This embodiment of incorporation into the compositions spheroids charged with perfume, essential oils or their constituents, makes possible the formulation of products, having an external aqueous phase, particularly rich in these compounds, which until now was not possible to obtain.

Representative liposoluble cosmetic or dermo-pharmaceutical components which can be incorporated into the spheroids, include more or less liposoluble vitamins or pro-vitamins, such as vitamins A and E and their esters, esters of vitamin C, carotenoids, anti-radicular substances, antiseptics, anti-acne or anti-pellicular agents, U.V. filters, keratolytic agents such as salicylic acid or its derivatives or salts, molecules active on pigmentation, on inflammation, such as the esters of zinc or copper and fatty acids, emollient fatty esters, oils of mineral, animal, vegetable or synthetic origin, substitutes or components of sebum such as squalane, squalene or ceramides, cholesterol, biologic extracts or hair dyes, etc.

It is also possible to incorporate in these spheres softening or lubricating charges for the skin such as talc, polyamide microballs, or on the other hand particles intended to produce polishing or an abrasion of the skin or teeth, such as polyethylene powders or other plastic materials, vegetable, cellulosic or lignic fragments, or mineral particles such as silica powders.

The spheroids can also contain a small percentage of other conventional components for cosmetic or dermo-pharmaceutical lipidic phases, such as antioxidants, preservatives and dyes.

Finally these spheroids can themselves contain other spheres, capsules or molecular carrier systems whose size can range from a few angstroms up to a few hundreds of microns or any other microcapsular or micromatrix system itself containing active principles. The total formula is then pluricompartmented, each compartment being unconnected.

According to a preferred embodiment of the present invention, the compositions contain, in suspension, hydrated spheroids charged with the aid of various cosmetic or pharmaceutical components which provide a particular interest in the case of components incompatible amongst themselves, such as perfumes or unsaturated oils and metals or metallic oxides.

The present invention also relates to a process for preparing the compositions such as defined above, this process comprising incorporating, with stirring, solid spheroids, charged or not charged, in the continuous phase so as to form a suspension and then submitting the resulting suspension to a step called "maturation" for a determined period of time and at a controlled temperature, the treatment being a function of the nature of the hydrophilic lipidic substance employed to form the spheroids and the nature of the external aqueous phase.

This latter "maturation" step causes hydration of spheroids and consequently their swelling and softening.

This phenomenon, which is macroscopically visible, is accompanied by an increase in the diameter and an optional modification of the color and opacity of the spheroids, principally when they are charged with a coloring substance or a pigment.

The "maturation" step is generally carried out at a temperature between 15° and 80° C. and for a period of time ranging from 1 hour to 15 days.

The solid spheroids can be prepared by any conventional granulation or spheronization method, hot or cold.

For example, cold solidification of droplets of melted hydrophilic lipidic substance involves maintaining the droplets in motion in a nonsolvent liquid, such as water, or by cooling using a cold gas, the droplets of the pulverized hydrophilic lipidic substance, projected onto a rotating disc, or extruded, using a cold gas or by hot granulation around a solid ring in a turbine, or by a bed of fluidized air, or in a planetary mixer, by passage across a vibrating wire gage or grill, by grinding, molding or injection or under pressure in molds, or by cutting or division of a solid lipidic mass.

The cold preparation methods, or those requiring little heat, are generally preferred when the cosmetic or dermopharmaceutical components, included in the hydrophilic lipidic substance, are sensitive vis-a-vis temperature or oxidation. The cooling of melted droplets is obtained preferably by a gas rather than with water.

According to the selected process and fabrication parameters the resulting solid spheroids are perfectly measured either with respect to size distribution or more or less diameter spread.

The solid spheroids can be handled industrially without taking any particular precautions. Their introduction into the external phase can be carried out directly in the final packaging, without the maturation step having taken place.

The compositions according to the invention are, as previously indicated, gels, lotions or emulsions of the water-in-oil or oil-in-water type, but preferably are gels.

The gels in which the spheroids are incorporated are obtained using a gelling agent which is generally present in an amount ranging from 0.02 to 70 percent by weight relative to the total weight of the gel. The spheroids can be charged or noncharged hydrated spheroids.

Representative particularly appropriate gelling agents for the formation of the gels according to the invention include principally carboxyvinyl polymers, such as the "CARBOPOLS", neutralized by a mineral or organic base (soda or triethanolamine), polysaccharide gelling agents such as alginates, xanthan gums, cellulose derivatives, or even gelatin or mineral gelling agents such as bentones or modified silicas.

These gels can also contain in the continuous aqueous phase various water-soluble cosmetically or dermo-pharmaceutically acceptable adjuvants and in particular dyes, hydrating agents, biologic extracts, vitamins or aminated acids.

The following nonlimiting examples of the preparation of charged or noncharged solid spheroids as well as several examples of the preparation of gels are given as an illustration of the invention.

DETAILED DESCRIPTION OF THE INVENTION

Preparation of Solid Spheroids

The hydrophilic lipidic substance plus optional active component aggregate is prepared hot. The solid component of the hydrophilic lipidic substance is melted at a temperature 2° to 3° C. above the melting point of the hydrophilic lipidic substance having the highest melting point. The other components, beginning with the less sensitive one, are then added.

The mixture is maintained at a temperature 2° to 3° C. above the temperature of the solidification zone. The sensitive or volatile components are added last. The solid are added to the melted mixture at the end and are maintained with stirring. They can optionally be "pasted" by a fraction of the melted hydrophilic lipidic substance before their incorporation into the whole of the mixture.

When the mixture is homogenized, the melted mass is pulverized in the upper portion of a vertical column of cold air. The melted lipid droplets fall by gravity all while being cooled.

The solidified droplets are recovered at the bottom of the column.

In accordance with another process, it is also possible to cause the melted lipidic mass to flow into an aqueous phase brought to the same temperature and maintained with circular stirring: the lipidic mixture disperses in the form of spherical droplets. A gelling agent is then added to the medium, which is cooled with stirring. In this case, the preparation of the spheroids is effected simultaneously with their incorporation into the final external medium.

By employing one or the other of these methods, noncharged and charged solid spheroids of various substances have been prepared in accordance with the following examples:

(1) Example of Noncharged Spheroids

| | |
|---|---|
| Stearyl alcohol having 2 moles of ethylene oxide, sold by ICI under the tradename "BRIJ 72" | 100 g |

Average particle size: 1000 μm (2) Example of Spheroids Charged with Petrolatum

| | |
|---|---|
| Petrolatum oil | 10 g |
| Petrolatum | 19 g |
| Glycerol monodipalmitostearate | 60 g |
| Interesterified oleic glyceride, sold under the tradename "LABRAFIL M 2735 CS" by Gattefosse | 10 g |
| Perfume | 1 g |

Average particle size: 1500 μm (ivory color)

(3) Example of Spheroids Charged with Pigments

Example 3A

| Yellow iron oxide | 3 g |
|---|---|
| Red iron oxide | 1.5 g |
| Black iron oxide | 0.5 g |
| Titanium dioxide | 15 g |
| Palm oil/interesterified hydrogenated palmiste | 10 g |
| Hydrophilic beeswax | 60 g |
| Carrot maceration in soya oil | 10 g |

Average particle size: 500 μm (brown color)

Example 3B

| Yellow iron oxide | 1 g |
|---|---|
| Red iron oxide | 1 g |
| Titanium dioxide | 15 g |
| Palm oil/interesterified hydrogenated palmiste | 10 g |
| Hydrophilic beeswax | 60 g |
| Carrot maceration in soya oil | 10 g |

Average particle size: 500 μm (ocher color)

Example 3C

| Titanium dioxide | 20 g |
|---|---|
| Palm oil/interesterified hydrogenated palmiste | 10 g |
| hydrophilic beeswax | 60 g |
| Carrot maceration in soya oil | 10 g |

Average particle size: 500 μm (white color)

Example 3D

| Glycerol monodipalmitostearate | 68.75 g |
|---|---|
| Liquid fraction of karite butter | 15 g |
| Miglyol gel | 8 g |
| Ocher iron oxide | 1.4 g |
| Red brown iron oxide | 0.8 g |
| Black iron oxide | 0.2 g |
| Titanium dioxide | 5.6 g |
| BHT | 0.05 g |
| Preservative | 0.2 g |

Average particle size: between 600 and 800 μm (purple color)

Example 3E

| Glycerol monodipalmitostearate | 68.75 g |
|---|---|
| Liquid fraction of karite butter | 15 g |
| Miglyol gel | 8 g |
| Chromium dioxide | 0.5 g |
| Titanium dioxide | 7.5 g |
| BHT | 0.05 g |
| Preservative | 0.2 g |

Average particle size: between 400 and 500 μm (light green color)

(4) Example of Spheroids Charged with Perfume

| Perfume concentrate | 30 g |
|---|---|
| Glycerol monodipalmitostearate | 54 g |
| Polyethyleneglycol monodipalmitostearate | 15.75 g |
| Butyl hydroxytoluene | 0.05 g |
| Preservative | 0.2 g |

Average particle size: 1,000 μm (pale yellow color)

(5) Example of Spheroids Charged with Soya unsaponifiables

| Oily extract or soya unsaponifiables | 40 g |
|---|---|
| Glycerol monodipalmitostearate | 55 g |
| Myristic alcohol | 1.748 g |
| Vitamin A palmitate | 3 g |
| DC Green 6 | 0.002 g |
| Butylhydroxytoluene | 0.05 g |
| Preservative | 0.2 g |

Average particle size: between 500 and 1,200 μm (green color)

(6) Example of Spheroids Charged with a Cicatrizing Agent

| Sorbitan monostearate | 88 g |
|---|---|
| Oily extract of calendula | 10 g |
| α-bisabolol | 1 g |
| Blue nacre | 1 g |

Average particle size: 500 μm, hard, blue colored spheroids

EXAMPLES OF PREPARING COMPOSITIONS

Example A—Preparation of a Tonic Makeup Removed Gel

In an appropriate flask 80 grams of a gel having the following composition are packaged:

| "CARBOPOL 940", sold by Goodrich | 0.15 g |
|---|---|
| Sodium hydroxide, sufficient for pH = 6.5 | |
| Glycerine | 3 g |
| Witch hazel water | 20 g |
| Rose water | 29 g |
| FD and C Blue 1 | 0.002 g |
| Preservative | 0.02 g |
| Water, sufficient amount for | 100 g |

To this gel there are incorporated, with stirring, 20 g of the solid spheroids charged with petrolatum and obtained in accordance with Example 2.

The flask is then submitted to a maturation step by placing it in an enclosure at 45° C. for 3 days.

At the end of this maturation period a bluish transparent fluid gel, containing white colored hydrated spheroids having an average diameter of 2,500 μm, is obtained.

This gel constitutes an excellent makeup remover which does not require rinsing off with water or with a tonic. It does not leave fatty residues on the skin nor does it cause an uncomfortable sensation due to a drying effect.

Example B—Preparation of a Makeup Foundation

In an appropriate flask 91 g of a gel having the following composition are packaged.

| "CARBOPOL 940", sold by Goodrich | 0.25 g |
|---|---|
| Triethanolamine, sufficient amount for pH = 6.5 | |
| Glycerine | 4 g |
| Preservative | 0.2 g |
| Water, sufficient amount for | 100 g |

To this gel there are incorporated, with stirring, 3 g of solid spheroids charged with pigments obtained in accordance with Example 3A, 3 g of solid spheroids charged with pigments obtained in accordance with Example 3B and 3 g of solid spheroids charged with pigments obtained in accordance with Example 3C.

The flask thus packaged is then submitted to a maturation step by placing it in an appropriate enclosure at a temperature of 37° C. for 4 days.

At the end of this maturation step a transparent gel, containing in dispersion the hydrated spheroids of various colors (light brown, ocher and white) having a diameter of about 1,000 μm, is obtained.

When applied to the face this gel is rapidly homogenized under finger pressure. The excipient is rapidly absorbed and the pigments produce a homogeneous matte makeup effect which is particularly well suited for oily skin.

Example C—Preparation of a Perfumed Gel

In an appropriate flask 95 g of a gel having the following composition are packaged:

| "CARBOPOL 940", sold by Goodrich | 0.3 g |
|---|---|
| Triethanolamine, sufficient amount for pH = 6.5 | |
| Sodium containing methylparaben | 0.2 g |
| Glycerine | 4 g |
| Distilled water, sufficient amount for | 100 g |

There is then incorporated into the flask 5 g of solid spheroids charged with perfume obtained in accordance with Example 4 using a planetary mixer.

After maturation for a week in an appropriate enclosure at 20° C., there is obtained a transparent gel containing therein well blended hydrated spheroids having a very pale yellow color having an average diameter of 2,000 μm which are easily emulsified on the skin with the gel.

This perfumed product can be applied over the entire body.

Example D—Preparation of a Skin Care Gel

In an appropriate flask 96 g of a gel having the following composition are packaged:

| "CARBOPOL 940", sold by Goodrich | 0.35 g |
|---|---|
| Sodium containing methylparaben, sufficient amount | |
| Distilled water, sufficient amount for | 100 g |

To this pre-gel there are incorporated 4 g of solid spheroids charged with soya unsaponifiables obtained in accordance with Example 5 using a planetary mixer. Then with continued stirring, the pre-gel is adjusted to a pH close to neutral by adding 0.35 g of triethanolamine. Stirring is terminated when the gel reaches a stable viscosity.

After maturation for 4 days at 37° C. in an appropriate enclosure, there is obtained a transparent gel containing therein hydrated spheroids, having a diameter ranging from 700 to 2,000 μm and a very pale green color, which immediately emulsify on the skin during application.

Example E—Preparation of a Water-in-Oil Emulsion

In an appropriate flask 96 g of an emulsion having the following composition are packaged:

| Petrolatum oil | 6 g |
|---|---|
| Petrolatum | 6 g |
| Paraffin | 3 g |
| Partial glyceride of isostearic acid | 6 g |
| Combination of caprylic/capric triglycerides and bentone | 15 g |
| Volatile silicone oil (pentamer) | 6 g |
| Glycerine | 5 g |
| Magnesium sulfate having 7 molecules of water | 1 g |
| Preservative, sufficient amount | |
| Distilled water, sufficient amount for | 100 g |

This emulsion is prepared in accordance with conventionally known techniques and is provided in the form of a white cream.

There are incorporated therein 4 g of solid spheroids charged with a cicatrizing agent obtained in accordance with Example 6.

After a week of maturation, the spheroids have swollen and are transformed into hydrated spheroids, having a diameter of about 800 μm, a bluish color and a well blended consistency. The spheroids remain perfectly individualized in the cream.

Their cicatrizing power adds to the softening and protective effect of the water-in-oil emulsion. This product is particularly recommended for dry and irritated skin.

Example F—Preparation of an Oil-in-Water Emulsion

In an appropriate flask 95 g of an emulsion having the following composition are packaged:

| Ricin oil | 8 g |
|---|---|
| Jojoba oil | 5 g |
| Glycerol monodipalmitostearate | 6 g |
| "CARBOPOL 940", sold by Goodrich | 0.2 g |
| Soda | 0.1 g |
| Preservative, sufficient amount | |
| Antioxidant, sufficient amount | |
| Distilled water, sufficient amount for | 100 g |

This emulsion is prepared in accordance with conventionally known techniques and is provided in the form of a white cream.

There are then incorporated therein, with stirring, 5 g of solid spheroids charged with soya unsaponifiables obtained in accordance with Example 5.

The whole is submitted to a maturation step for 48 hours at 37° C.

The resulting product is an oil-in-water emulsion having a light texture, containing pale green hydrated spheroids having a diameter between 700 and 2,000 μm. The spheroids are well individualized and emulsify on the skin with the cream during application.

The hydrated spheroids provide a supplemental supply of active components relative to the cream.

Example G—Preparation of a Lotion

To 85 g of a lotion having the following composition:

| Rosewater | 10 g |
|---|---|
| Blue water | 10 g |
| Glycerine | 5 g |
| Preservative, sufficient amount | |
| Dye, sufficient amount | |
| Distilled water, sufficient amount for | 100 g | there are incorporated 15 g of solid spheroids charged with soya unsaponifiables obtained in accordance with Example 5.

The whole is submitted to maturation for 48 hours at 37° C.

The resulting product is a lotion which contains, in suspension, pale green hydrated spheroids having a diameter between 700 and 2,000 μm. The spheroids are well individualized, noncoalescent and are easily emulsified with the lotion during application on the skin.

These hydrated spheroids enrich the lotion with lipidic active components and improve its comfort.

Example H—Preparation of a Makeup Gel

In 95.5 g of gel having the following composition:

| "CARBOPOL 940", sold by Goodrich | 0.3 g |
|---|---|
| Sodium containing methylparaben | 0.2 g |
| Glycerine | 5 g |
| Sunscreen agent | 0.1 g |
| Distilled water, sufficient amount for | 100 g | there are incorporated, with stirring, 3.5 g of the solid spheroids charged with pigments obtained in accordance with Example 3D and 1 g of the solid spheroids charged with pigments obtained in accordance with Example 3E.

The gel, having in suspension the solid spheroids, is packaged in a transparent pliable tube.

The tube is then submitted to maturation for 5 days at 37° C.

There is thus obtained a transparent gel containing therein large creamy spheres, rich in pigments and having a rose brown color and a diameter of about 1,000 to 1,500 µm. The gel also contains small pale green spheres of the same consistency having a diameter of about 700 to 900 µm and having a color correction function.

Exerting pressure on the tube dispenses the gel without interfering with the integrity of the spheres. When the product is applied to the skin, the totality of the pigments is emulsified and homogenized under finger pressure into a light cream, thereby effecting makeup of a color having an agreeable consistency.

I claim:

1. A process for preparing an aqueous composition for application to the skin, said composition having emollient and lubricating properties and comprising creamy spheroids in suspension in a continuous water-containing external phase, said phase comprising (a) water or a mixture of water and a hydroxylated organic solvent, said mixture containing at least 50 percent of water or (b) a gel, said gel containing a gelling agent present in an amount ranging from 0.02 to 70 percent by weight relative to the total weight of said composition, said creamy spheroids having an average particle diameter ranging from 100 to 5,000 µm, said creamy spheroids resulting from the hydration of solid spheroids of a hydrophilic lipidic substance having a melting point greater than 20° C. and a hydration capacity such that said solid spheroids absorb 1.3 to 8 times their weight of water, and said hydrophilic lipidic substance being selected from the group consisting of:

(1) a $C_{12}$–$C_{24}$ fatty alcohol having a melting point between 20° and 80° C. and having a hydroxyl index ranging from 100 to 300, (2) a partial ester of a $C_{12}$–$C_{24}$ fatty acid with a polyol or polyol oligomer, said partial ester having a melting point ranging from 20° to 80° C. and a hydroxyl index ranging from 50 to 500, (3) an oxyethylenated fatty body having 2 to 50 moles of ethylene oxide per mole of fatty body and having a melting point of 20° to 80° C., (4) a product resulting from the alcoholysis reaction between a natural triglyceride and a polyoxethylenated glycol, having a melting point ranging from 20° to 80° C., and hydroxyl index ranging from 50 to 500, (5) a phospholipid and sphingolipid having a melting point ranging from 20° to 80° C., and hydroxyl index ranging from 50 to 500, and (6) an amphiphilic silicone having a melting point ranging from 20° to 80° C. and having 2 to 50 moles of ethylene oxide per mole of product, said spheroids being present in an amount ranging from 0.1 to 50 percent by weight based on the total weight of said composition;

said process comprising incorporating in said continuous phase, solid spheroids of said hydrophilic lipidic substance, said spheroids being charged or not, so as to form a suspension and submitting the resulting composition to a maturation step so as to cause hydration and swelling of said spheroids.

2. The process of claim 1 wherein said spheroids are incorporated in an amount ranging from 0.1 to 50 percent by weight based on the total weight of the composition.

3. The process of claim 1 wherein said spheroids are incorporated in an amount ranging form 1.5 to 10 percent by weight based on the total weight of the composition.

4. The process of claim 1 wherein said maturation step is effected at a temperature ranging from 15° to 80° C. for a period of time ranging from 1 hour to 15 days.

* * * * *